US010563154B2

(12) United States Patent
Faure et al.

(10) Patent No.: US 10,563,154 B2
(45) Date of Patent: Feb. 18, 2020

(54) DISINFECTING AQUEOUS FOAM, PROCESS FOR PREPARING SAME AND USE THEREOF

(71) Applicant: COMMISSARIAT A L'ENERGIE ATOMIQUE ET AUX ENERGIES ALTERNATIVES, Paris (FR)

(72) Inventors: Sylvain Faure, Venasque (FR); Esther Le Toquin, Villeneuve les Avignon (FR); Fabienne Gas, Saint Laurent de Carnols (FR)

(73) Assignee: COMMISSARIAT A L'ENERGIE ATOMIQUE ET AUX ENERGIES ALTERNATIVES, Paris (FR)

(*) Notice: Subject to any disclaimer, the term of this patent is extended or adjusted under 35 U.S.C. 154(b) by 97 days.

(21) Appl. No.: 15/736,666

(22) PCT Filed: Jun. 15, 2016

(86) PCT No.: PCT/EP2016/063790
§ 371 (c)(1),
(2) Date: Dec. 14, 2017

(87) PCT Pub. No.: WO2016/202879
PCT Pub. Date: Dec. 22, 2016

(65) Prior Publication Data
US 2018/0187131 A1    Jul. 5, 2018

(30) Foreign Application Priority Data
Jun. 16, 2015 (FR) .................... 15 55501

(51) Int. Cl.
C11D 3/22 (2006.01)
C11D 3/39 (2006.01)
(Continued)

(52) U.S. Cl.
CPC ............... C11D 3/48 (2013.01); A61L 2/235 (2013.01); C11D 1/662 (2013.01); C11D 1/825 (2013.01); C11D 3/0094 (2013.01); C11D 3/222 (2013.01)

(58) Field of Classification Search
CPC ......... C11D 1/662; C11D 3/0094; C11D 3/22; C11D 3/39; C11D 3/48; B08B 3/04
See application file for complete search history.

(56) References Cited

U.S. PATENT DOCUMENTS 6,336,977 B1   1/2002  Menke et al.
7,276,468 B1  10/2007  Tucker
(Continued)

FOREIGN PATENT DOCUMENTS

FR   2 841 802 A1   1/2004
FR   2 912 668 A1   8/2008
(Continued)

OTHER PUBLICATIONS

International Search Report dated Sep. 13, 2016, in PCT/EP2016/063790 filed Jun. 15, 2016.
French Search Report dated Jun. 6, 2016 in French Application 1555501 filed Jun. 16, 2015.
(Continued)

Primary Examiner — Brian P Mruk
(74) Attorney, Agent, or Firm — Oblon, McClelland, Maier & Neustadt, L.L.P.

(57) ABSTRACT

The present invention relates to a foam consisting of a dispersion of gas bubbles in a foaming solution comprising, per litre of solution, (i) from 0.05 to 1.5% by weight of one or more foaming organic surfactant(s), (ii) from 0.05% to 0.8% by weight of one or more organic gelling or viscosifying agent(s), (iii) from 1% to 14% by volume of one or more disinfecting agent(s) and (iv) water, said foam having (Continued)

Figure 1A:
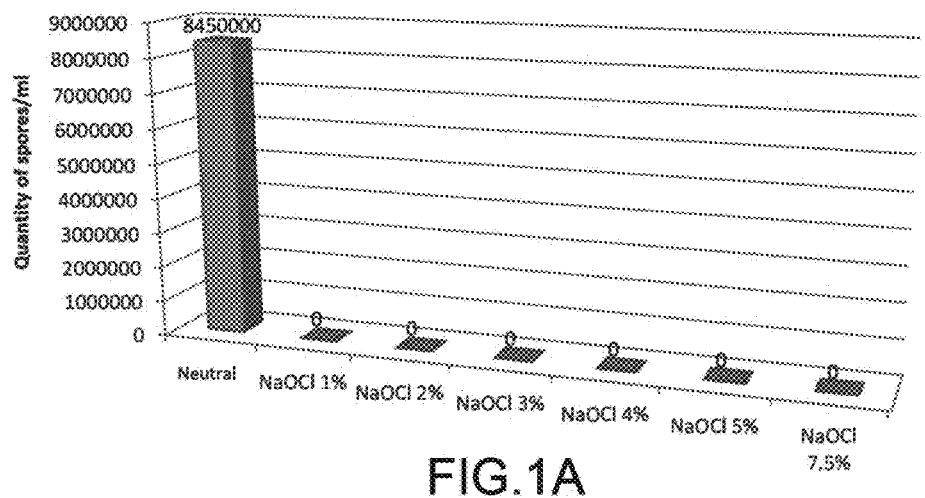

an expansion between 12.5 and 50. The present invention also relates to the use of such a foam for biological decontamination.

12 Claims, 10 Drawing Sheets

(51) Int. Cl.

| | | |
|---|---|---|
| *C11D 3/48* | (2006.01) |
| *B08B 3/04* | (2006.01) |
| *A61L 2/235* | (2006.01) |
| *C11D 1/66* | (2006.01) |
| *C11D 3/00* | (2006.01) |
| *C11D 1/825* | (2006.01) |

(56) References Cited

U.S. PATENT DOCUMENTS

| | | | |
|---|---|---|---|
| 7,662,754 B2 * | 2/2010 | Faure | C11D 1/662 |
| | | | 134/42 |
| 2006/0211592 A1 * | 9/2006 | Faure | C11D 1/662 |
| | | | 510/421 |
| 2010/0069281 A1 | 3/2010 | Guignot et al. | |
| 2010/0111877 A1 | 5/2010 | Biering et al. | |

FOREIGN PATENT DOCUMENTS

| | | |
|---|---|---|
| FR | 2 980 367 A1 | 3/2013 |
| WO | 01/45505 A2 | 6/2001 |
| WO | 02/43847 A1 | 6/2002 |
| WO | 2004/008463 A2 | 1/2004 |

OTHER PUBLICATIONS

ETF Holdings Inc., "Material Safety Data Sheet Name of Finished Solution: EasyDECON DF200-531X", Internet <URL: http://www.easydecon.com/easydecon/EasyDECON%20DF200%20MSDS.pdf> . Alabama 2008; 2 pages.
ETF Holdings Inc., "Performance Data", Internet <URL: http://www.easydecon.com/easydecon/FactSheete248.html>, Alabama 2011, 4 pages.
Allen Vanguard et al., "CASCAD Decontamination Foam", Internet <URL: http://reports.hms-online.org/ViewProduct.aspx?CategoryId=175&ProductId=721>, 2009, 3 pages.
"Biological Agent Decontamination Technology Testing" Office of Research and Development, National Homeland Security Research Center, 2010, 87 pages.
J.T. Davies, "A Quantitative Kinetic Theory of Emulsion Type. I. Physical Chemistry of the Emulsifying Agent", Proceedings of the International Congress of Surface Activity, 1957, 13 pages.
"Regulation (EU) No. 528/2012 of the European Parliament and of the Council: Concerning the Making Available on the Market and Use of Biocidal Products", Official Journal of the European Union, May 22, 2012, 123 pages.
U.S. Appl. No. 14/399,155, filed Nov. 5, 2014, US 2015-0110560 A1, Sylvain Faure.
U.S. Appl. No. 15/525,718, filed May 10, 2017, Sylvain Faure.

* cited by examiner

DISINFECTING AQUEOUS FOAM, PROCESS FOR PREPARING SAME AND USE THEREOF

FIELD OF THE INVENTION

The present invention relates to the biological decontamination and particularly the treatment of materials and/or facilities contaminated with pathogenic agents such as bacteria, viruses, and fungi. More particularly, the present invention is applicable to the decontamination/disinfection of surfaces contaminated with such pathogenic agents.

Indeed, the present invention relates to a controlled-moisture, gelled or viscosified, aqueous foam, containing at least one disinfecting agent as well as the use thereof for treating surfaces contaminated with pathogenic agents.

STATE OF THE RELATED ART

The use of biological agents as weapons is not a novel idea. History shows that such a use has existed since before the discovery of micro-organisms. Whether through the contamination of wells with infected corpses or the distribution of blankets of smallpox sufferers to spread the infection, history shows that the use of pathogenic agents as a weapon is an age-old concept. More recently, the anthrax spore booby-trapped letter attack that occurred in the United Stated in the autumn of 2001 raised awareness among European and American public opinion on the reality of the bioterrorist threat.

In the hypothetical case of a biological accident or attack, the priority for the authorities is to limit the effects on the civilian population. This limiting involves the rapid decontamination of exposed infrastructures in order to prevent agent propagation and restore buildings to their use without delay without any persisting exposure risk. Some difficult-to-access contaminated areas, such as, for example, ventilating ducts or wastewater discharge pipes, need to be rapidly decontaminated to prevent any spread of pathogenic agents. Therefore, there is a need on the market for means for decontaminating these areas. Such decontaminating means should be suitable for use by filling an enclosed or semi-enclosed space or for spraying onto vertical and horizontal walls. Furthermore, as identification is not always possible and the response needs to be rapid, the decontamination solution must, for its part, be effective against a wide range of biological agents.

A plurality of biological and/or chemical decontamination foams exist, used in the field of Nuclear, Radiological, Biological, Chemical (NRBC) risks.

A first decontamination form DF-100 was developed by Sandia National Laboratories. The formulation of this solution comprises a surfactant, a reagent compound, i.e. liquid hydrogen peroxide and water. A second solution was developed: DF-200 or EasyDECON® 200 [1]. This solution is an enhanced version of DF-100, as it further contains a bleaching activator which is glycerol diacetate. The latter compound makes it possible to increase the reaction rate, enhance the reaction yield and do away with the need to adjust the pH. This foam is multi-purpose as it is effective for neutralising chemical warfare agents such as sarin, mustard gas, O-ethyl S-[2-(diisopropylamino)ethyl] methylphosphonothioate (or VX) and soman, industrial chemical toxins and biological agents such as *B. anthracis* and *Y. pestis*. It is not corrosive and the use thereof does not create harmful by-products. As furnished in the patent application US 2007/0249509 [2], the complete formulation of DF-200 foam consists, as a percentage by weight with respect to the total weight of the formulation, of:

- 1.8% benzalkonium chloride (cationic surfactant);
- 0.5% ADOGEN 477™ (cationic hydrotrope);
- 1.1% hexylene glycol (solvent);
- 0.4% 1-dodecanol (fatty acid);
- 12% sorbitol (sorbent additive which acts as a drying agent to produce a granulated form);
- 4.7% of a mixture of potassium carbonate and potassium bicarbonate, used as a strong base;
- 1.8% glycerol diacetate (water-soluble bleaching activator);
- 4.6% polyethylene glycol (water-soluble polymer particularly used to increase foam stability);
- 7.8% hydrogen peroxide urea (decontaminating agent) and
- 65.3% water.

The performances of the DF-100 and DF-200 solutions on chemical and biological agents such as, for example, *Bacillus globigii* (simulating Anthrax), *Bacillus anthracis* and *Yersinia pestis* are accessible on the Internet [3].

CASCAD™ Surface Decontamination Foam (CASCAD™ SDF), marketed by Allen-Vanguard, has the properties of decontaminating buildings contaminated with biological and chemical agents, as well as radioactive particles, and of confining an explosion. This solution was developed to decontaminate buildings without damaging the various contaminated materials. It is the enhanced version of CASCAD™ (for "Canadian Aqueous System for Chemical/biological Agent Decontamination") decontamination solution [4]. The latter is a solution developed to decontaminate vessels, aircrafts and vehicles in the event of suspected or proven contamination.

CASCAD™ SDF foam has been optimised for use over a longer period of time and under more restrictive weather conditions. It is presented in the form of a powder which can be dispensed, after adding water, in liquid form or in foam form according to a wide range of dispersion equipment. After application and a sufficient contact time, the solution may be rinsed or displaced using pumps.

CASCAD™ SDF foam is produced by mixing and reacting two liquid solutions together. The latter are prepared using three separate reagents which have the following chemical compositions:

- GPA-2100 (decontaminant): solid reagent in powder form consisting of a sodium salt of dichloroisocyanuric acid (70 to 100% by weight);
- GPA-2100 (buffer): solid reagent in powder form consisting of sodium tetraborate (10 to 30% by weight), sodium hydroxide (1 to 5% by weight) and sodium carbonate (40 to 65% by weight); and
- GCE-2000 (surfactant): liquid reagent consisting of myristic sodium sulphate (10 to 30% by weight), sodium olefin sulphonate (C14-16) (10 to 30% by weight), denatured ethanol (3 to 9% by weight), alcohols (C10-16) (5 to 10% by weight), sodium sulphate (3 to 7% by weight), sodium xylene sulphonate (1 to 5% by weight) and a mixture of sodium and ammonium salts with water and a co-solvent (quantity greater than 9% by weight).

A method for preparing CASCAD™ SDF foam is particularly provided in Annex B of [5]. This report proposes a comparative study of the decontamination efficacy of a plurality of decontamination solutions including DF-200, CASCAD™ SDF and bleach solution, on various materials.

This study relates to six decontamination solutions:
- pH-Amended Bleach used in liquid form and composed of 5% sodium hypochlorite, water and 5% acetic acid to adjust the pH;
- CASCAD™ SDF (Allen-Vanguard) used in foam form;
- Decon Green used in liquid form, the active agent being hydrogen peroxide;
- EasyDECON® 200 (DF-200) (EFT Holdings, Inc.) used in liquid form;
- Spor-Klenz® RTU (STERIS Corporation) used in liquid form, the active agents being hydrogen peroxide and peracetic acid;
- Peridox® RTU (CET, LLC) used in liquid form, the active agents being hydrogen peroxide and peracetic add.

The results obtained in terms of the decontamination efficacy with respect to *Bacillus anthracis* spores and presented in [5] demonstrate that porous materials such as concrete, asphalt and treated wood are more difficult to decontaminate than non-porous materials such as glass, stainless steel, aluminium, porcelain and granite. The most effective solution for decontaminating spores is CASCAD™ SDF foam. It is effective both on porous and non-porous materials. EasyDECON 200 solution and the bleach-based solution are not effective on porous materials such as asphalt and treated wood. For these three solutions, no damage was observed on the materials after 60 min of contact time and 7 days after the spore count.

In summary, the foams according to the prior art are versatile on chemical and biological agents. They are mostly used by spraying onto the surfaces to be treated. However, it should be noted that the foaming solutions from which they are prepared have numerous constituents which is not only costly but also results in long preparation processes. Finally, the expansion of these foams is not specified and therefore not controlled.

The inventors set themselves the aim of developing a foam suitable for use for treating surfaces contaminated with biological agents, that is easy to use and, regardless of the surface to be treated, requires no structure, or costly reagent and generates very little effluent once the treatment has been carried out.

DESCRIPTION OF THE INVENTION

The aims set and further aims are achieved by the invention which relates to a controlled-moisture aqueous foam and method for treating and disinfecting contaminated surfaces.

The present invention is an aqueous foam with moisture controlled by a specific generator. These physicochemical properties enable the stability thereof over time in foam form by means of the use in the formulation of a viscosifying agent. The expansion control by the generator makes it possible to obtain stable foams that are effective against pathogenic agents with a moisture percentage between 2% and 8%, and preferentially between 4% and 5%.

The use and retrieval of the foam according to the invention are novel. Indeed, the controlled expansion between 12.5 and 50 and advantageously between 20 and 25 allows use by spraying or spreading in a "layer" (or floating) of a foam that is stable and adherent to inclined, horizontal or vertical walls, floors and ceilings. The foam according to the present invention may also be used for filling enclosed or semi-enclosed environments optionally of variable and large volume. This foam may be retrieved by suction or by merely allowing to evaporate, the evaporation leaving non-toxic traces.

Therefore, the present invention relates to a foam suitable for evaporation and suction which represents a completely novel concept with regard to foams according to the prior art. Furthermore, in terms of liquid effluents, a foam suitable for suction generates very little, and a form suitable for evaporation generates none.

More particularly, the present invention relates to a foam consisting of a dispersion of gas bubbles in a foaming solution comprising, per litre of solution:
- from 0.05% to 1.5% by weight of a foaming organic surfactant or of a mixture of foaming organic surfactants,
- from 0.05% to 0.8% by weight of an organic gelling or viscosifying agent or of a mixture of organic gelling or viscosifying agents,
- from 1% to 14% by volume of a disinfecting agent or of a mixture of disinfecting agents and
- water, said foam having an expansion between 12.5 and 50.

Due to the composition thereof, the disinfecting aqueous foam according to the present invention has the advantages of controlled-lifetime foams conventionally used in radioactive decontamination treatment (see, in this respect, the international application WO 2004/008463 [6]). However, the disinfecting aqueous foam according to the present invention differs from the foams described in the international application WO 2004/008463 by the absence of radiological decontamination agent and by the expansion thereof.

Note that, in one particular embodiment of the invention, the foaming aqueous solution used for preparing the disinfecting aqueous foam according to the present invention only contains, in addition to water, three types of compounds which corresponds to a simplified formulation with respect to the formulations of the foams according to the prior art. Such a foaming aqueous solution therefore consists of
- from 0.05% to 1.5% by weight of a foaming organic surfactant or of a mixture of foaming organic surfactants,
- from 0.05% to 0.8% by weight of an organic gelling or viscosifying agent or of a mixture of organic gelling or viscosifying agents,
- from 1% to 14% by volume of a disinfecting agent or of a mixture of disinfecting agents and
- water, The foaming solution used for preparing the disinfecting aqueous foam comprises, as a solvent, water, thus justifying the description foaming aqueous solution. The term "water" denotes tap water, deionised water or distilled water. Advantageously, the disinfecting aqueous foam according to the invention may be a neutral, acidic or basic foam, according to the disinfecting agent(s) contained therein and the pH conditions required for satisfactory disinfecting efficacy thereof. Those skilled in the art will be able to determine the most suitable pH and modify the pH of the foaming aqueous solution accordingly.

The disinfecting aqueous foam according to the invention is a controlled-expansion and therefore a controlled-moisture foam. By way of reminder, a foam is frequently characterised by the expansion thereof defined, under normal temperature and pressure conditions, by the following relation (I):

$$F = (Vol_{gas} + Vol_{liquid})/Vol_{liquid} = Vol_{foam}/Vol_{liquid} \quad (I)$$

Consequently, the moisture of a foam corresponds to the reciprocal of the expansion thereof and therefore is defined by the ratio $Vol_{liquid}/Vol_{foam}$.

The disinfecting aqueous foams according to the present invention have an expansion between 12.5 and 50, particularly between 15 and 30 and, in particular, between 20 and 25, which corresponds to a liquid fraction or moisture of the foam between 2 and 8%, particularly between 3.33 and 6.67% and, in particular, between 4 and 5%. Note that the liquid volume ($Vol_{liquid}$) in the above ratios corresponds to the volumes of the various compounds initially mixed to prepare the foaming aqueous solution and, in particular to the sum of the volume of the foaming organic surfactant(s), the volume of the organic gelling or viscosifying agent(s), of the disinfecting agent(s) and the volume of water.

The foaming aqueous solution generating the disinfecting aqueous foam according to the invention comprises at least one foaming organic surfactant. The term "organic surfactant" denotes an organic molecule including a lipophilic (apolar) part and a hydrophilic (polar) part. The term "foaming organic surfactant" denotes an organic surfactant as defined above further having a hydrophilic-lipophilic balance (HLB) between 3 and 8. By way of reminder, the HLB value of a surfactant may be readily obtained by means of the Davies formula [7] and the HLB charts for different chemical groups, available for those skilled in the art.

More particularly, the foaming aqueous solution forming the disinfecting aqueous foam according to the invention may comprise a single foaming organic surfactant or a mixture of at least two foaming organic surfactants chosen from non-ionic foaming surfactants, anionic foaming surfactants, cationic foaming surfactants, amphoteric surfactants, Bolaform type structural surfactants, Gemini type structural surfactants and polymeric surfactants.

Advantageously, the foaming aqueous solution used within the scope of the present invention comprises a single foaming organic surfactant or a mixture of at least two foaming organic surfactants chosen from non-ionic foaming surfactants, anionic foaming surfactants and cationic foaming surfactants. In the mixtures of foaming organic surfactants, at least two surfactants are chosen in the same family or in two different families chosen from among non-ionic foaming surfactants, anionic foaming surfactants and cationic foaming surfactants.

By way of reminder, non-ionic (or neutral) surfactants are compounds wherein the surfactant properties, particularly the hydrophily, are provided by non-charged functional groups such as an alcohol, an ether, an ester or an amide, and may contain heteroatoms such as nitrogen or oxygen. Due to the low hydrophilic contribution of these functions, the foaming non-ionic surfactant compounds are generally polyfunctional. Within the scope of the present invention, the foaming non-ionic surfactants are particularly chosen from alkyl alkoxylates; fatty alcohol alkoxylates; fatty amine alkoxylates; fatty acid alkoxylates; oxo alcohol alkoxylates; alkylphenol alkoxylates; alkyl ethoxylates; fatty acid ethoxylates; fatty amine ethoxylates; fatty acid ethoxylates; oxo alcohol ethoxylates; alkylphenol ethoxylates such as, for example, octylphenol and nonylphenol ethoxylates; alcohols, α-diols, polyethoxylated and poly-propoxylated alkylphenols having a fatty chain including, for example, 8 to 18 carbon atoms, the number of ethylene oxide or propylene oxide groups optionally being particularly from 2 to 50; polyethylene and polypropylene oxide complex polymers; ethylene and propylene oxide copolymers; polyethylene and polypropylene oxide block copolymers such as, for example, POE-POP-POE triblock copolymers; ethylene and propylene oxide condensates on fatty alcohols; polyethoxylated fatty amides having, preferably, 2 to 30 moles of ethylene oxide; polyethoxylated ethers having, preferably, 2 to 30 moles of ethylene oxide; monoesters (monolaurate, monomyristate, monostearate, monopalmitate, monooleate, etc.) and polyesters of fatty acids and glycerol; polyglycerolated fatty amides comprising on average from 1 to S and, more especially, from 1.5 to 4 glycerol groups; oxyethylenated sorbitan fatty acid esters including 2 to 30 moles of ethylene oxide; monoesters (monolaurate, monomyristate, monostearate, monopalmitate, monooleate, etc.) and polyesters of fatty acids and sorbitan, monoesters of sorbitan polyoxyethylene; sucrose esters of fatty acids; polyethyleneglycol esters of fatty acids; alkyl polyglucosides; N-alkyl glucamine derivatives and amine oxides such as alkyl($C_{10}$-$C_{14}$) amine oxides or N-acylaminopropylmorpholine oxides; polyols (surfactants derived from sugars) in particular glucose alkylates such as for example glucose hexanate; surfactants derived from glucoside (sorbitol laurate) or polyols such as glycerolated alcohol ethers; alkanolamides and mixtures thereof. More particularly, by way of foaming non-ionic surfactants, it is possible to use the foaming non-ionic surfactants described in the international application WO 2004/008463 [6]. Such a surfactant is, for example, chosen in the family of alkylpolyglucosides or alkylpolyetherglucosides, biodegradable natural derivatives of glucose. These are for example "ORAMIX CG-110" from SEPPIC, or "Glucopon 215 CS" from COGNIS.

Anionic surfactants are surfactants wherein the hydrophilic part is negatively charged. A foaming anionic surfactant suitable for use within the scope of the present invention is typically chosen in the group consisting of sulphuric acid esters, phosphoric acid esters, alkyl or aryl sulphonates, alkyl or aryl sulphates, alkyl or aryl phosphates, alkyl or aryl sulphosuccinates or alkyl or aryl sarcosinates associated with a counterion such as an ammonium ion ($NH4^+$), a quaternary ammonium such as tetrabutylammonium, and cations and particularly alkaline cations, said cations being such as $Na^+$, $Li^+$, $Ca^+$, $Mg^{2+}$, $Zn^{2+}$ and $K^+$. By way of foaming anionic surfactants, it is, for example, possible to use tetraethylammonium paratoluenesulphonate, sodium dodecylsulphate (or SDS), sodium laurylsarcosinate (or sarcosyl), sodium palmitate, sodium stearate, sodium myristate, sodium di(2-ethylhexyl) sulphosuccinate, methylbenzene sulphonate and ethylbenzene sulphonate.

Cationic surfactants have at least one hydrocarbon chain and a polar head, the hydrophilic part of said agent being positively charged. A foaming cationic surfactant suitable for use within the scope of the present invention is advantageously chosen from quaternary ammoniums comprising at least one $C_4$-$C_{22}$ aliphatic chain associated with an anionic counterion chosen particularly from boron derivative such as tetrafluoroborate or halide ions such as $F^-$, $Br^-$, $I^-$ or $Cl^-$. By way of foaming cationic surfactants suitable for use, mention may be made of tetrabutylammonium chloride, tetradecylammonium bromide, tetradecyltrimethyl ammonium bromide (TTAB), alkylpyridinium halides carrying an aliphatic chain and alkylammonium halides.

In one particular embodiment, the foaming organic surfactant(s) is/are chosen in the group consisting of carboxylic acid salts, sulphonic acid salts, sulphate salts, sulphuric acid ester salts, phosphoric acid ester salts, alkylpolyglucosides and amine oxides.

In the foaming aqueous solution forming the disinfecting aqueous foam according to the present invention, the surfactant or the mixture of at least two surfactants is present at a rate of 0.05 to 1.5% by weight, particularly from 0.08 to 1.3% by weight and, in particular, from 0.1 to 1.1% by weight per litre of solution.

Furthermore, the foaming aqueous solution forming the disinfecting aqueous foam according to the present invention comprises, in addition to the surfactant(s) cited above, an organic gelling or viscosifying agent or a mixture of at least two organic gelling or viscosifying agents in a content between 0.05% and 0.8% by weight, particularly from 0.1 to 0.5% by weight and, in particular, from 0.15 to 0.3% by weight per litre of solution.

Advantageously, such an organic gelling agent is a biodegradable, pseudoplastic agent enabling the foam to be readily sprayable and have a lifetime between 30 min and 6 hours and therefore suitable for the period of biological decontamination and use.

This or these gelling and/or viscosifying agent(s) is/are, more particularly, chosen from water-soluble polymers, hydrocolloids, heteropolysaccharides such as, for example, trisaccharide branched-chain polyglucoside polymers, cellulose derivatives and polysaccharides such as polysaccharides containing glucose as a single monomer. By way of particular examples, the gelling or viscosifying agent(s) suitable for use within the scope of the present invention is/are chosen in the group consisting of xanthan gum, guar gum, agar-agar, carrageenan, sodium alginate, caseinate, gelatin, pectin, starch, cellulose, 2-hydroxyethylcellulose (HEC) and chitosan.

Finally, the foaming aqueous solution forming the disinfecting aqueous foam according to the present invention comprises, in addition to the foaming organic surfactant(s) and the gelling or viscosifying agent(s) cited above, a disinfecting agent or a mixture of at least two disinfecting agents at a content between 1% and 14% by volume.

The disinfecting agent or the mixture of disinfecting agents may be present in the foaming aqueous solution at a quantity between 1 and 10% by volume, particularly between 2 and 7.5% by volume and, in particular, of the order of 5% (i.e. 5%±1%) by volume per litre of solution. These specific ranges are particularly used for surfaces which are neither made of metal, or steel and for which no reaction with the disinfecting agent(s) has been demonstrated.

Alternatively and particularly for metal or steel surfaces, the content of disinfecting agent or mixture of at least two disinfecting agents is typically between 5% and 14% by volume and, in particular, of the order of 12% (i.e. 12%±1%) by volume per litre of solution. In this scenario, the disinfecting agent(s) may react with such surfaces such as aluminium surfaces.

The disinfecting agent(s) suitable for use within the scope of the present invention belong(s) to the biocidal products as defined by the regulations concerning the marketing and use of biocidal products (EU Regulation No. 528/2012 of 22 May 2012 [8]). These biocidal products represent all of the substances and mixtures, consisting of one or a plurality of active molecule(s), with the intention of destroying, deterring, rendering harmless, preventing the action of, or otherwise exerting a controlling effect on, any harmful living organisms by chemical or biological action. These products are divided, according to the applications thereof, into four groups which are (i) disinfecting agents, (ii) protective products aimed at preventing microbial and algal development, (iii) pest control products and (iv) other biocidal products such as antifouling products or embalming and taxidermist products.

Disinfecting agents are products or processes used for disinfecting or decontaminating contaminated materials and can be applied to inert surfaces, living tissue or foodstuffs. As such, disinfecting agents are used for treating in particular medical devices, floors and surfaces such as metal, concrete, brick, ceramic, wood and plastic which are materials used in critical infrastructures as well as sensitive equipment.

The efficacy of disinfecting agents is dependent on the spectrum of action on the different types of biological agents. As such, bactericidal agents (action on bacteria), fungicidal agents (action on fungi), virucidal agents (action on viruses) and sporicidal agents (action on spores) are defined. Furthermore, each disinfecting agent has a number of performance criteria, such as (i') the rate of efficacy thereof, (ii') the decontamination efficacy thereof which is measured by a reduction factor of an initial contaminant population under the effect of the disinfectant (initial population/final population after treatment) or by the reduction in $\log_{10}$ of this factor and (iii') the compatibility thereof with construction materials. Disinfecting agents are therefore classified according to the disinfection efficacy thereof and the terms high-, intermediate- and low-level disinfection disinfecting agents are used.

Within the scope of the present invention, the disinfecting agent(s) used is/are chosen from high-level disinfection disinfecting agents i.e. disinfecting agents having a factor (initial contaminant population/final population after treatment) greater than $10^6$. Advantageously, these factors are chosen from chlorinated products, aldehydes and oxidants.

Chlorinated products are disinfecting agents with a broad spectrum of activity since they are bactericidal, virucidal, fungicidal and sporicidal. The action time thereof is rapid and equal to the drying time thereof. However, they are subject to factors influencing the activity thereof such as the pH and temperature. Furthermore, the activity thereof is inhibited in the presence of heavy metal ions, a biofilm, dissolved organic matter, at low temperature, at low pH, or in the presence of UV radiation. They are used as surface, liquid effluent and equipment disinfectants.

By way of examples of chlorinated products suitable for use as disinfecting agents within the scope of the present invention, mention may be made of chlorine, sodium hypochlorite (bleach solution) and chlorine dioxide. Note that the pH of sodium hypochlorite which is 11 on average may be adjusted so that it is between 5 and 8. Indeed, at this pH, sodium hypochlorite is more effective as a disinfectant and probably becomes less corrosive for materials.

Aldehydes have a broad spectrum of activity as they are bactericidal, fungicidal, virucidal and sporicidal. They are used in liquid or gas form for disinfecting surfaces, equipment, premises and medical devices. They have the action of inducing micro-organism nucleic acid and protein denaturation.

By way of examples of aldehydes suitable for use as a disinfecting agent within the scope of the present invention, mention may be made of glutaraldehyde and succinic aldehyde.

Oxidants have a broad spectrum of activity as they are bactericidal, fungicidal, virucidal and sporicidal. The efficacy thereof is superior at an acidic pH and they are inhibited by the presence of organic matter. They have the action of destroying organic membranes. They are mainly used in vapour form for disinfecting surfaces and equipment.

By way of examples of oxidants suitable for use as a disinfecting agent within the scope of the present invention, mention may be made of peroxides such as hydrogen peroxide; activated peroxides such as hydrogen peroxide+ bicarbonate, hydrogen peroxide+urea, hydrogen peroxide+ peracetic acid and hydrogen peroxide+iron (Fenton's reagent); hydroperoxycarbonates; peracetic acid; sodium perborate; sodium percarbonate optionally perhydrated; sodium peroxysilicate; sodium peroxypyrophosphate; sodium peroxysilicate and aryloxides such as arylbenzenesulphonates.

In one particular embodiment of the invention, the foaming disinfecting agent(s) is/are chosen in the group consisting of chlorinated products and oxidants. More particularly, the foaming disinfecting agent(s) is sodium hypochlorite and hydrogen peroxide.

The gas used for generating the disinfecting aqueous foam according to the invention may be any gas. It may particularly be chosen in the group consisting of air, oxygen, carbon dioxide, helium, argon and nitrogen. Advantageously, the gas used within the scope of the present invention is air. As such, the disinfecting aqueous foam according to the invention consists of a dispersion of air bubbles in a foaming solution as defined above.

By way of particular examples of disinfecting aqueous foam according to the invention, mention may be made of:

(1) a dispersion of bubbles of gas and particularly of air in a foaming solution comprising (or consisting of) per litre of solution:
 from 0.1 to 1.1% by weight of a foaming organic surfactant or of a mixture of foaming organic surfactants,
 from 0.15% to 0.3% by weight of an organic gelling or viscosifying agent or of a mixture of organic gelling or viscosifying agents,
 from 2% to 7.5% by volume and particularly of the order of 5% by volume of a disinfecting agent or of a mixture of disinfecting agents and
 water;

(2) a dispersion of bubbles of gas and particularly of air in a foaming solution comprising (or consisting of) per litre of solution:
 from 0.1 to 1.1% by weight of a foaming organic surfactant or a mixture of foaming organic surfactants,
 from 0.15% to 0.3% by weight of an organic gelling or viscosifying agent or of a mixture of organic gelling or viscosifying agents,
 from 5% to 14% by volume and particularly of the order of 12% by volume of a disinfecting agent or of a mixture of disinfecting agents and
 water;

(3) a dispersion of bubbles of gas and particularly of air in a foaming solution comprising (or consisting of) per litre of solution:
 from 0.1 to 1.1% by weight of an alkylpolyglucoside,
 from 0.15% to 0.3% by weight of xanthan gum,
 from 2% to 7.5% by volume and particularly of the order of 5% by volume of sodium hypochlorite or hydrogen peroxide and
 water;

(4) a dispersion of bubbles of gas and particularly of air in a foaming solution comprising (or consisting of) per litre of solution:
 from 0.1 to 1.1% by weight of an alkylpolyglucoside,
 from 0.15% to 0.3% by weight of xanthan gum,
 from 5% to 14% by volume and particularly of the order of 12% by volume of sodium hypochlorite or hydrogen peroxide and
 water;
 the expansion of these foams being as defined above.

The present invention relates to a method for preparing the disinfecting aqueous foam as defined above. The latter may be readily prepared, at ambient temperature (i.e. at a temperature of the order of 23° C.±5° C.), using techniques known to those skilled in the art.

The first step of this preparation method consists of mixing together water, the foaming organic surfactant(s), the organic gelling or viscosifying agent(s) or the disinfecting agent(s), prior to foam generation. This mixing may be performed by adding the components in one go, by group or in succession. In one particular embodiment, it may be envisaged to prepare a first solution by mixing together water, the foaming organic surfactant(s) or the organic gelling or viscosifying agent(s) and only adding the disinfecting agent(s) to this solution immediately prior to generating the foam.

The second step of this preparation method consists of generating the foam. This step may be performed by means of any system for generating foam according to the prior art and known to those skilled in the art. It consists of any device for gas-liquid mixing, particularly by mechanical stirring, by bubbling, by static mixer optionally containing beads, by microbead tube foam generator or devices described in the international application WO 02/043847 [9], or any other device particularly nozzle or venturi systems enabling high flow rates between 1 and 1000 m$^3$/hr. More particularly, the invention advantageously uses a foam generator suitable for controlling the moisture of the foam generated. This moisture control is performed by measuring the mixed solution and air flow rate. The formulations according to the invention make it possible to readily obtain a foam with the latter type of generator wherein the moisture is between 2 and 8%, particularly between 3.33 and 6.67% and, in particular, between 4 and 5%.

The present invention relates to the use of a disinfecting aqueous foam as defined above for treating a surface likely to be contaminated with at least one biological agent. More particularly, the present invention relates to a method for treating a surface likely to be contaminated with at least one biological agent consisting of contacting said surface with a disinfecting aqueous foam.

The term "treating a surface likely to be contaminated with at least one biological agent" denotes within the scope of the present invention reducing the quantity of biological agents present on the surface prior to the treatment according to the invention. This reduction may involve eliminating or destroying these agents and/or the conversion thereof into less harmful elements. As such, the expression "treatment of a surface" is equivalent and interchangeable with the expressions "disinfection of a surface" and "biological decontamination of a surface".

Any surface likely to be contaminated by one or a plurality of biological agent(s) may undergo a treatment method according to the present invention. The term "surface" denotes the external part of an object or solid body, limiting same in all directions. It is possible, for the same object (or same solid body), to conceptually define different surfaces. The invention is applicable to any type of surface regardless of the geometry thereof. The latter may be simple, such as a perfectly planar surface, or complex, such as rough surface, or have unobstructed cavities, regardless of the material forming the surface and the rest of the object on which it depends.

Advantageously, within the scope of the present invention, the surface of the object to be treated may be an inorganic or organic surface and particularly a surface made of metal such as aluminium, metal alloy, steel and particularly stainless steel, tinplate, silicon, glass generally containing silicates, silica glass, ceramic, brick, porcelain, cement, concrete, asphalt, stone, granite, wood, clay, plastic or any one of the combinations thereof.

The surface to be treated or the object for which the surface is to be treated according to the method according to the present invention may have any size, shape and orientation. It may consist of large surfaces such as a road or the wall, ceiling and/or floor of a large infrastructure such as building, airport, underground railway or hotel, intermediate-sized installations such as an industrial object like a machine implemented in the agri-food industry, vehicle, framework, aircraft, tank, restaurant kitchen, cold store, sanitary block or container, and small-sized installations such as medical devices, pipes, or a weapon.

The term "biological agent" denotes natural micro-organisms such as bacteria, archaea, parasites, protozoa, fungi, yeasts or viruses, the toxins produced or not by such micro-organisms, protein type pathogenic agents such as prions and genetically modified micro-organisms.

Figure 11A:
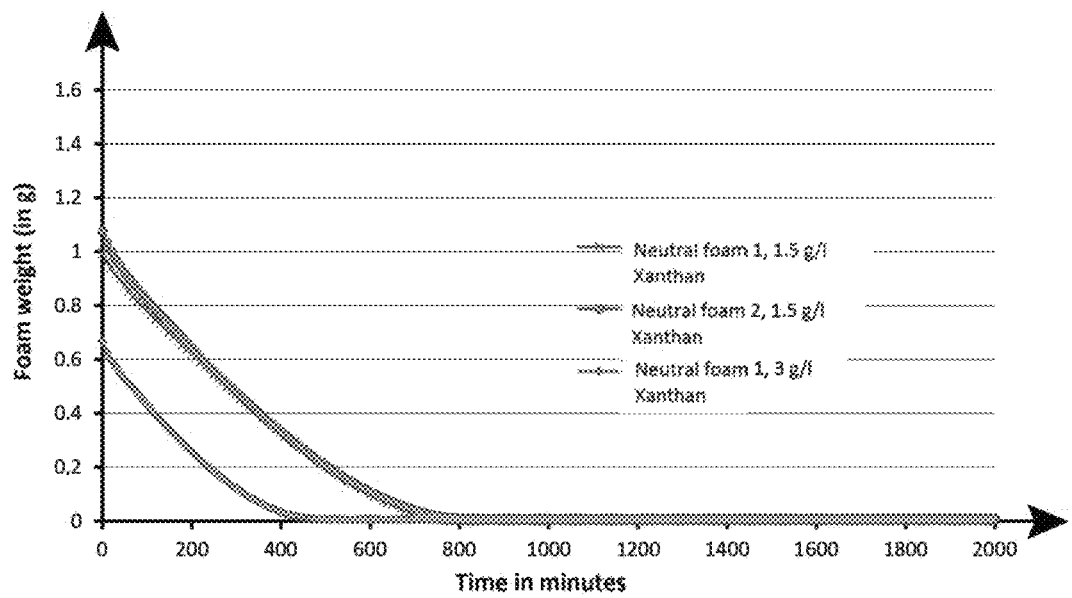
Figure 11B:
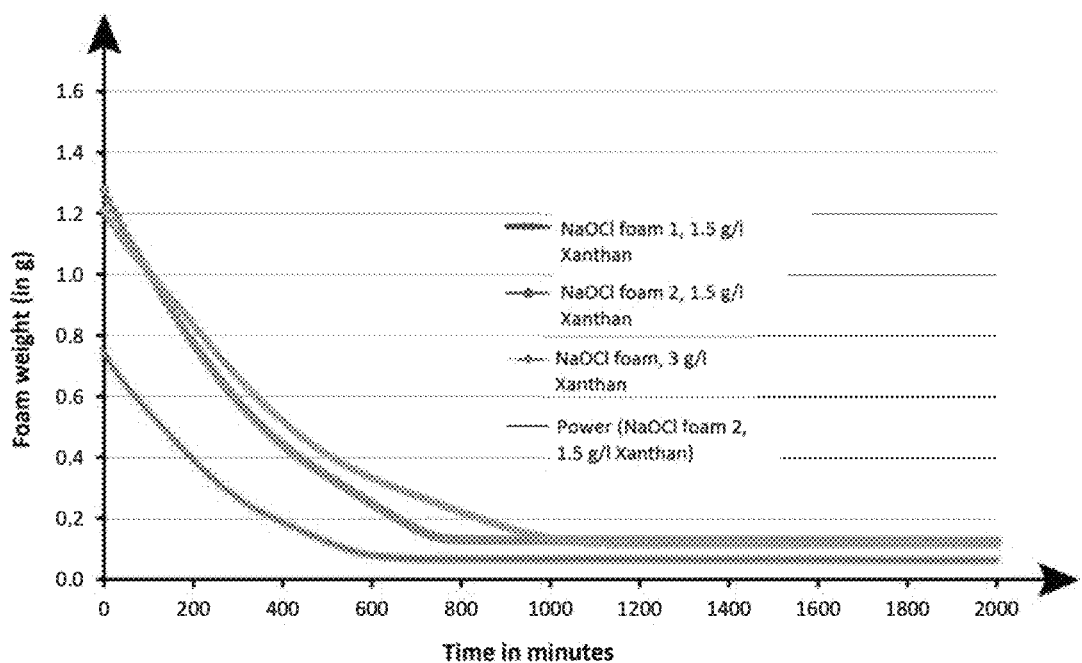
Figure 11C:
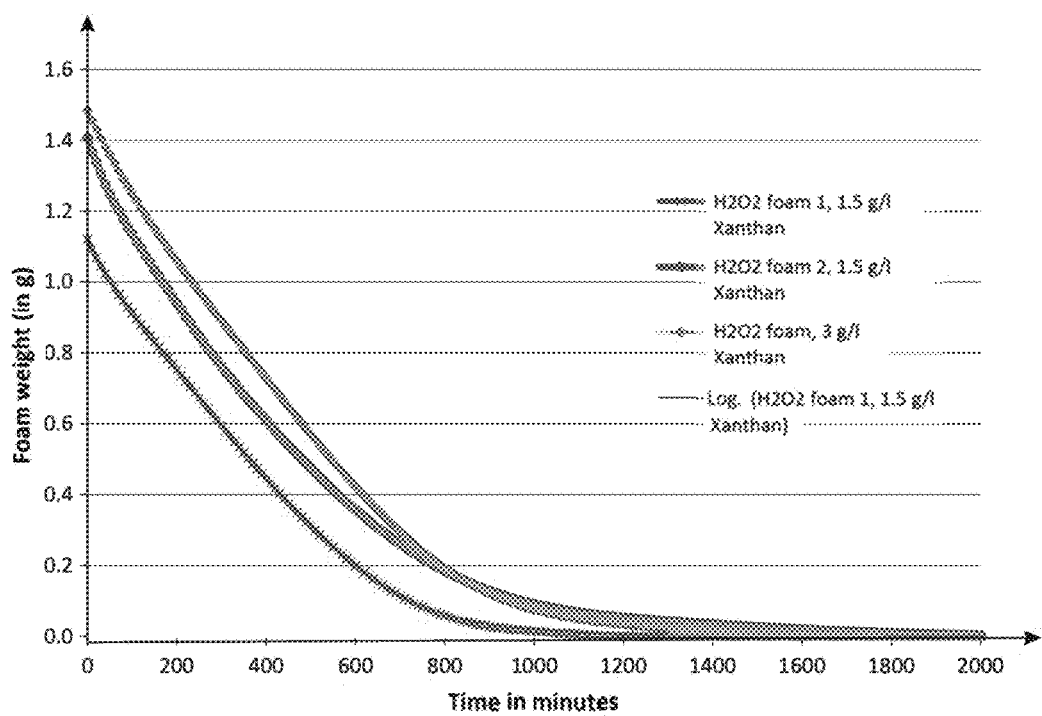

By way of particular and non-exhaustive examples of biological species likely to be eliminated by the method according to the invention, mention may be made of any type of micro-organisms such as bacteria, spores particularly *Bacillus anthracis* spores, viruses, fungi, yeasts and toxins. The species or biological species which are eliminated, destroyed, inactivated, by the foam according to the invention are essentially species or bio-toxic elements like pathogenic spores such as, for example, *Bacillus anthracis* spores, Gram − bacteria (such as for example *Yersinia pestis, Francisella tularensis, Pseudomonas aeruginosa, Salmonella thyphimurium* and *Legionella* sp) and Gram + bacteria (*Staphylococcus aureus, Clostridium* sp and *Streptococcus* sp), toxins such as, for example botulinum toxin, ricin or curcin, and viruses such as, for example, haemorrhagic fever viruses (such as Ebola for example) or coronaviruses (such as SARS for example).

In the method according to the invention, the contacting between the surface to be treated and the disinfecting aqueous foam is direct and may be carried out in various ways in "static" mode.

In a first embodiment, the contacting consists of applying, on the surface to be treated as defined above, the disinfecting aqueous foam as defined above. This first embodiment may involve application by spraying or by floating i.e. spreading in layers. In this first embodiment, the foam may be generated at the time of contacting (spraying) or, on the other hand, prior to this contacting (floating), in open or closed spaces. The layer of disinfecting aqueous foam sprayed or spread may be from 0.5 cm to 5 cm and advantageously from 1 to 2 cm.

In a second embodiment, the contacting consists of filling the structures having a surface to be treated as defined above with the disinfecting aqueous foam as defined above. These structures are particularly enclosed or semi-enclosed environments which can be of variable and large volume. This second embodiment is particularly suitable for treating sites and infrastructures that are accessible or inaccessible for humans such as ventilation pipes or items containing a plurality of non-movable components such as aircraft sanitary installations. Indeed, the foam limits liquid dead volumes, occupying the entire space and wetting all of the surfaces such as pipes, gratings or the gap between non-removable objects.

The contacting time ranges from a few minutes to the complete drying of the disinfecting aqueous foam. Advantageously, the contacting time is greater than 10 min, particularly greater than 20 min, and more particularly greater than 30 min, which is the time suitable for biological decontamination and use.

In the method according to the present invention, following the contacting step, said sprayed or floated foam is allowed to dry by evaporation or said foam used in filling mode is allowed to drain.

Furthermore, the method according to the present invention may have, following the contacting step, a step aimed at retrieving the foam or the residue of this foam. Advantageously, this retrieval may be performed using suction. In the event of foam remaining i.e. before complete drying, the latter is suctioned. On the other hand, if the liquid fraction of the foam is allowed to evaporate and therefore, if the foam has been allowed to dry, only non-toxic dried residue is present on the treated surface, and the latter is retrieved by suction or by wiping particularly using a wipe or a sponge. As this dried residue is non-toxic, it can also be left on the treated surface without retrieval thereof.

Further features and advantages of the present invention will emerge on reading the examples hereinafter given by way of illustration and not restriction and with reference to the appended figures.

BRIEF DESCRIPTION OF THE FIGURES

FIG. 1 shows the mean evaluation of the decontamination efficacy of a foam according to the invention containing different concentrations of sodium hypochlorite (FIG. 1A) or different concentrations of hydrogen peroxide (FIG. 1B).

FIG. 2 shows the mean rate of decontamination of a foam according to the invention containing sodium hypochlorite (FIG. 2A) or hydrogen peroxide (FIG. 2B).

FIG. 3 is a schematic representation of the experimental protocol used for evaluating the efficacy of a foam according to the invention on earthenware tiles.

FIG. 4 shows the evaluation of the decontamination efficacy of a foam according to the invention containing sodium hypochlorite or hydrogen peroxide on earthenware tiles (FIG. 4A) or on aluminium plate (FIG. 4B).

FIG. 5 shows the evaluation of the decontamination efficacy of a foam according to the invention containing sodium hypochlorite or hydrogen peroxide on vertical walls.

FIG. 6 shows the evaluation of the decontamination efficacy of a foam according to the invention containing sodium hypochlorite or hydrogen peroxide in filling mode.

FIG. 7 shows the evaluation of the decontamination efficacy of a foam according to the invention containing sodium hypochlorite or hydrogen peroxide and having different moisture percentages.

FIG. 8 shows the evaluation of the decontamination efficacy of a foam according to the invention containing sodium hypochlorite or hydrogen peroxide after ageing of the initial foaming solutions.

FIG. 9 shows a comparison of the foamability and drainage at t=0, t=1 wk and t=5 wks of storage, of a foam according to the invention containing sodium hypochlorite (FIG. 9A) or hydrogen peroxide (FIG. 9B).

FIG. 10 shows the slippage kinetics of an application of a foam according to the invention containing sodium hypochlorite or hydrogen peroxide on a wipe-off marker whiteboard.

FIG. 11 shows the evaporation kinetics of a neutral foam (FIG. 11A) or of a foam according to the invention containing sodium hypochlorite (FIG. 11B) or hydrogen peroxide (FIG. 11C), all of these foams optionally containing 1.5 g/l or 3 g/l of xanthan, as viscosifying agent.

DETAILED DESCRIPTION OF PARTICULAR EMBODIMENTS

I. Formulations Used for Foam.

The various formulations of the following solutions used during the tests presented hereinafter are contained in Table 1 hereinafter:

TABLE 1

| Name of formulation | Composition | Concentration per Litre of foaming solution |
|---|---|---|
| Neutral, 1.5 g/l of Xanthan | $H_2O$ | 839 ml/L |
| | Glucopon | 11 g/L |
| | 10 g/l Xanthan | 150 ml/L |
| Neutral, 2 g/l of Xanthan | $H_2O$ | 789 ml/L |
| | Glucopon | 11 g/L |
| | 10 g/l Xanthan | 200 ml/L |
| Neutral, 2.5 g/l of Xanthan | $H_2O$ | 739 ml/L |
| | Glucopon | 11 g/L |
| | 10 g/l Xanthan | 250 ml/L |
| Neutral, 3 g/l of Xanthan | $H_2O$ | 689 ml/L |
| | Glucopon | 11 g/L |
| | 10 g/l Xanthan | 300 ml/L |
| 1% NaOCl | $H_2O$ | 768 ml/L |
| | Glucopon | 11 g/L |
| | 10 g/l Xanthan | 150 ml/L |
| | 14% NaOCl | 71 ml/L |
| 2% NaOCl | $H_2O$ | 696 ml/L |
| | Glucopon | 11 g/L |
| | 10 g/l Xanthan | 150 ml/L |
| | 14% NaOCl | 143 ml/L |
| 3% NaOCl | $H_2O$ | 625 ml/L |
| | Glucopon | 11 g/L |
| | 10 g/l Xanthan | 150 ml/L |
| | 14% NaOCl | 214 ml/L |
| 4% NaOCl | $H_2O$ | 553 ml/L |
| | Glucopon | 11 g/L |
| | 10 g/l Xanthan | 150 ml/L |
| | 14% NaOCl | 286 ml/L |
| 5% NaOCl and 1.5 g/l Xanthan | $H_2O$ | 482 ml/L |
| | Glucopon | 11 ml/L |
| | 10 g/l Xanthan | 150 ml/L |
| | 14% NaOCl | 357 ml/L |
| 5% NaOCl and 2 g/l Xanthan | $H_2O$ | 431 ml/L |
| | Glucopon | 11 g/L |
| | 10 g/l Xanthan | 200 ml/L |
| | 14% NaOCl | 358 ml/L |
| 5% NaOCl and 2.5 g/l Xanthan | $H_2O$ | 381 ml/L |
| | Glucopon | 11 g/L |
| | 10 g/l Xanthan | 250 ml/L |
| | 14% NaOCl | 358 ml/L |
| 5% NaOCl and 3 g/l Xanthan | $H_2O$ | 331 ml/L |
| | Glucopon | 11 g/L |
| | 10 g/l Xanthan | 300 ml/L |
| | 14% NaOCl | 358 ml/L |
| 7.5% NaOCl | $H_2O$ | 303 ml/L |
| | Glucopon | 11 g/L |
| | 10 g/l Xanthan | 150 ml/L |
| | 14% NaOCl | 536 ml/L |
| 1% H2O2 | $H_2O$ | 806 ml/L |
| | Glucopon | 11 g/L |
| | 10 g/l Xanthan | 150 ml/L |
| | 30% H2O2 | 33 ml/L |
| 2% H2O2 | $H_2O$ | 772 ml/L |
| | Glucopon | 11 g/L |
| | 10 g/l Xanthan | 150 ml/L |
| | 30% H2O2 | 67 ml/L |
| 5% H2O2 and 1.5 g/l Xanthan | $H_2O$ | 672 ml/L |
| | Glucopon | 11 g/L |
| | 10 g/l Xanthan | 150 ml/L |
| | 30% H2O2 | 167 ml/L |
| H2O2 5% and 2 g/l Xanthan | $H_2O$ | 622 ml/L |
| | Glucopon | 11 g/L |
| | 10 g/l Xanthan | 200 ml/L |
| | 30% H2O2 | 167 ml/L |

TABLE 1-continued

| Name of formulation | Composition | Concentration per Litre of foaming solution |
|---|---|---|
| H2O2 5% and 2.5 g/l Xanthan | $H_2O$ | 572 ml/L |
| | Glucopon | 11 g/L |
| | 10 g/l Xanthan | 250 ml/L |
| | 30% H2O2 | 167 ml/L |
| 5% H2O2 and 3 g/l Xanthan | $H_2O$ | 523 ml/L |
| | Glucopon | 11 g/L |
| | 10 g/l Xanthan | 300 ml/L |
| | 30% H2O2 | 167 ml/L |
| 8% H2O2 | $H_2O$ | 574 ml/L |
| | Glucopon | 11 g/L |
| | 10 g/l Xanthan | 150 ml/L |
| | 30% H2O2 | 265 ml/L |

II. Biological Test Operating Protocol.

The tests are conducted with spores of *Bacillus thuringiensis* (Bt) which is a simili of *Bacillus anthracis*, in a biosafety cabinet (BSC) allocated to spores in an L2 microbiology laboratory. Petri dishes are contaminated with 100 µl of a solution containing $10^8$ spores of Bt/ml, i.e. a deposit of $10^7$ spores of Bt, which is allowed to dry completely under the hood (approximately 1 hr 30).

The foaming solutions are prepared in the laboratory with a static generator with beads. The foams are generated in a 2-litre beaker and then weighed to determine the moisture of the foam. The foams are then deposited onto the spores using a spatula.

The foams remain in contact with the spores with the dishes closed, for 1 hr to 1 hr 30 approximately or according to the test protocol (example for the biocidal action rate).

For each dish, the spores are taken up by depositing sterile water on several occasions and placed in one or a plurality of Falcon tubes made up to 45 ml. The Falcon tubes are centrifuged for 15 min at 4000 rpm.

The supernatant is removed and the pellet is re-suspended in 10 ml of liquid Luria-Broth (LB) nutrient broth, and then vortexed. If the same dish has required the use of a plurality of Falcon tubes, the tubes are combined into one. The Falcon tubes are placed in an incubator at 30° C. for 1 hr.

This incubation in LB medium enables the initiation of the desporulation of *Bacillus thuringiensis* spores which are converted into vegetative form at the correct temperature, and prolonged contacting of the substrate with the medium in order to retrieve a maximum number of spores present on the substrate. These vegetative forms may grow in the form of colonies on a solid nutrient medium (agar) in Petri dishes and thus be counted visually. This enables an estimation of the number of initial spores inactivated.

For each of the tubes incubated at 30° C., a series of ten-fold (factors of 10) successive dilutions by volume is produced with liquid LB (dilution to $10^8$ or to one hundred millionth). Finally, 1 ml is taken up into each of the tubes of each series of dilutions, and is then deposited onto the bottom of a sterile empty Petri dish.

LB agar medium is then poured into the dish (inoculation throughout). The dishes are then placed in an incubator at 30° C. for approximately 20 hrs. The colonies are counted one by one and a mean live spore count is calculated. A test containing no disinfectant, referred to as Neutral, is conducted at least once for each test, so as to check that the operating protocol has been applied correctly.

III. Evaluation of the Biocidal Efficacy of the Formulation.

III.1. Foams with Different Sodium Hypochlorite and Hydrogen Peroxide Concentrations.

Tests are conducted in order to determine the biocidal efficacy at different NaOCl and $H_2O_2$ concentrations. These tests are conducted according to the operating protocol described above and according to the formulations detailed above.

As such, three tests were conducted for 5% NaOCl, two tests for 5% $H_2O_2$ and one test for 1%, 2%, 3%, 4% and 7.5% NaOCl, as well as for 1% and 2% $H_2O_2$.

Figure 1B:
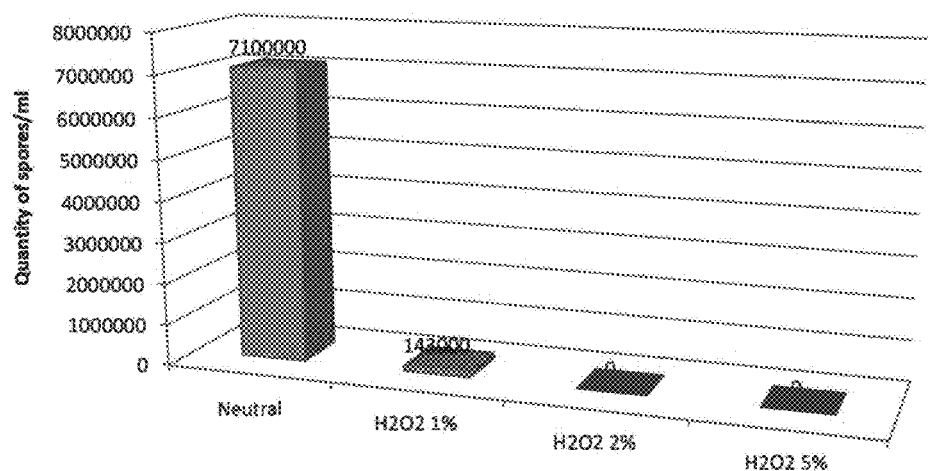

The results of these tests are shown in FIGS. 1A and 1B. It emerges that the foam according to the present invention with sodium hypochlorite is effective from a concentration of 1% sodium hypochlorite and that with hydrogen peroxide is effective from a concentration of 2% hydrogen peroxide.

III.2. Evaluation of Foam Decontamination Rates.

Tests are conducted in order to determine the biocidal efficacy rate of the NaOCl and $H_2O_2$ foams. These tests are conducted according to the operating protocol described above.

The contact time between the foam and the spores is measured with a timer. Foam/contamination contact times of 30 s, 5 min, 7 min, 10 min, 15 min, 30 min, 45 min and 1 hr were tested. However, it is necessary to take into account the irreducible treatment time due to the experimental protocol (foam retrieval and centrifugation) of approximately 20 min. The foam retrieved is diluted with sterilised water; therefore the disinfectant is at a lower concentration and the foam is broken down.

The number of reproductions of these tests is shown in Table 2 hereinafter:

TABLE 2

| Contact time | Number of 5% NaOCl tests | Number of 5% $H_2O_2$ tests |
|---|---|---|
| 30 seconds | 2 | 2 |
| 5 minutes | 1 | — |
| 7 minutes | 2 | 2 |
| 10 minutes | 1 | — |
| 13 minutes | 2 | 1 |
| 15 minutes | 2 | 3 |
| 30 minutes | 2 | 2 |
| 45 minutes | 2 | 2 |
| 60 minutes | 4 | 4 |

Figure 2A:
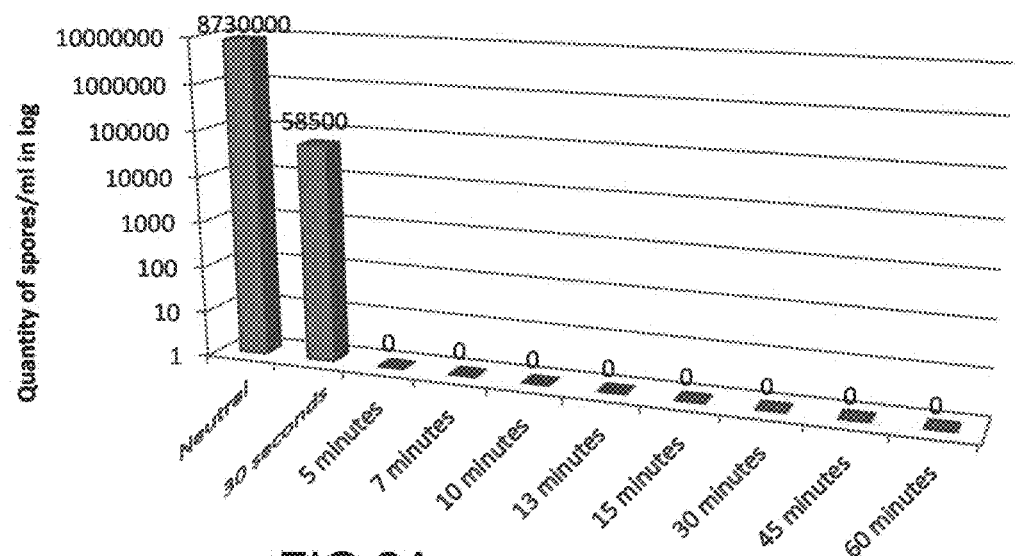
Figure 2B:
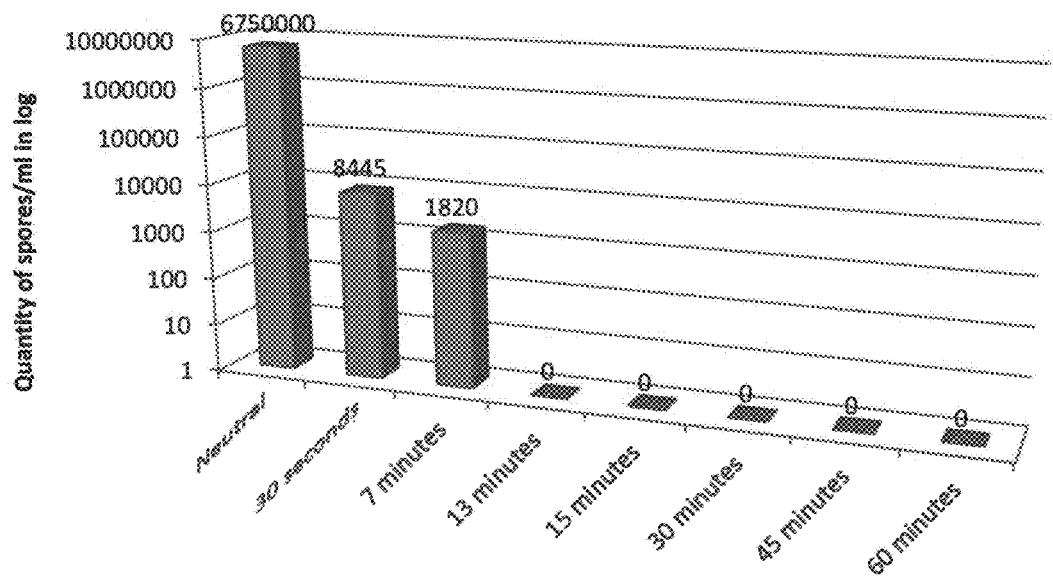

The results of these tests are shown in FIGS. 2A and 2B. As such, the foam containing 5% sodium hypochlorite and that containing 5% hydrogen peroxide neutralise all of the spores (approximately $10^7$ spores) from 5 min and 13 min of contact, respectively. It is necessary to add, to these contact times, the treatment time due to the experimental protocol, making it possible to state that the solutions are effective in 30 min; therefore, both disinfectants are effective in less than one hour.

III.3. Valuation of Decontamination Efficacy of Foams on Various Substrates.

Figure 3:
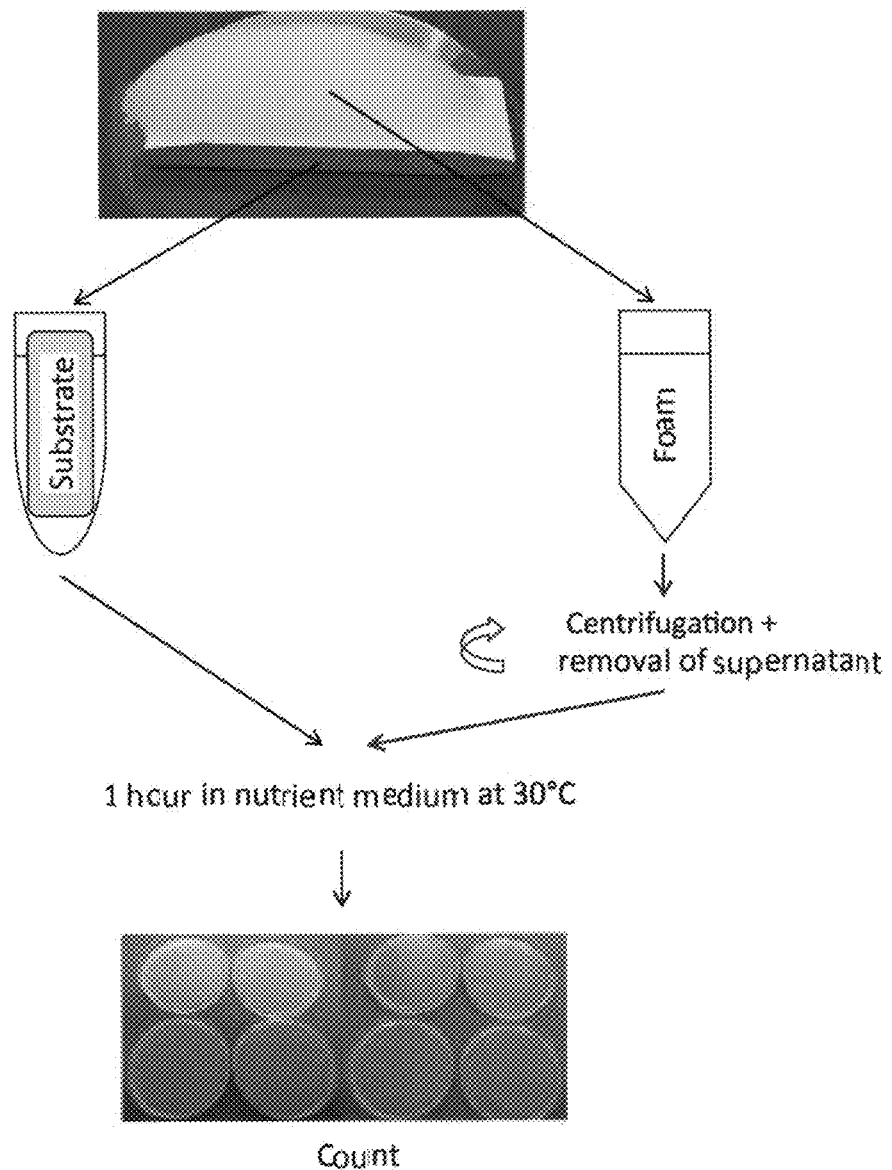
Figure 4A:
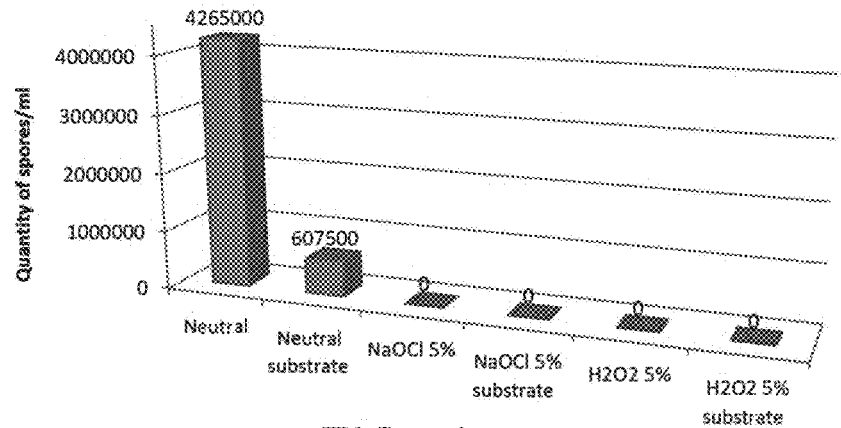
Figure 4B:
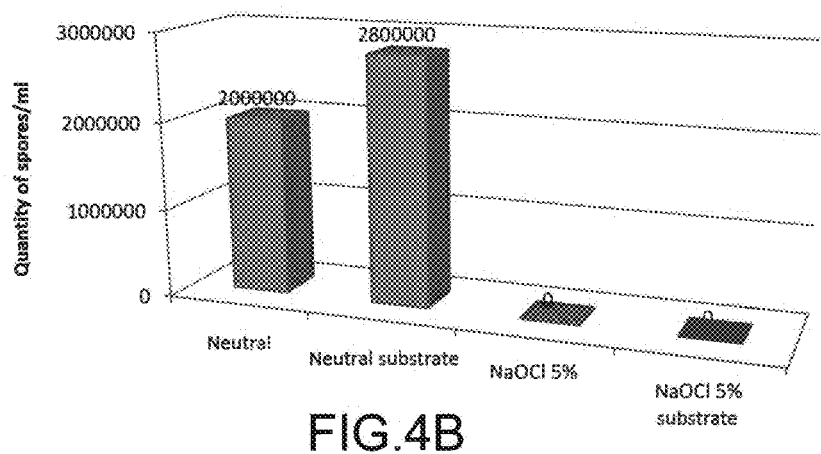
Figure 5:
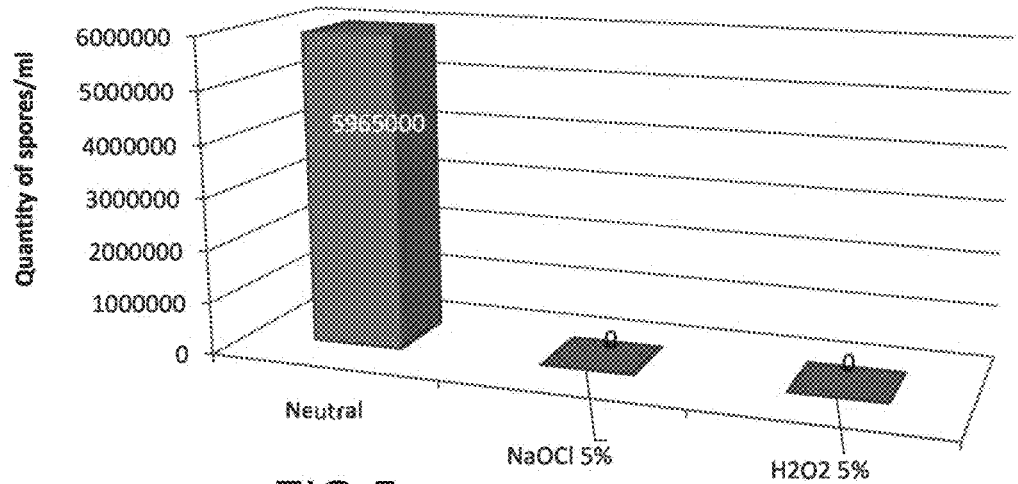
Figure 6:
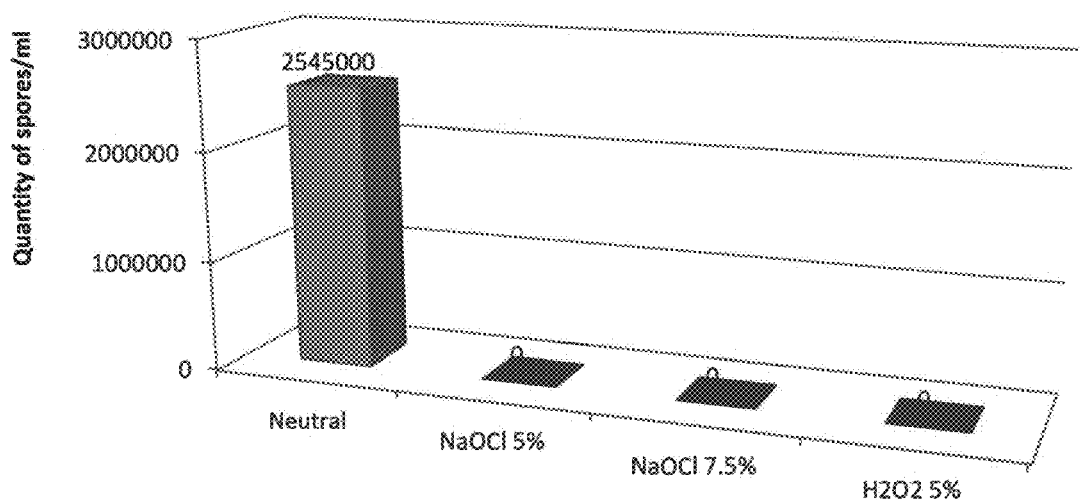

Tests are conducted in order to determine the biocidal efficacy of NaOCl and $H_2O_2$ foams on various materials. The tests follow the operating protocol described above apart from the depositions which are carried out on an earthenware tile or on an aluminium plate placed in a Petri dish with a contact time between the foam and the contaminated material of 30 min (FIG. 3).

The contaminated material is placed in a tube with 30 ml of liquid Luria-Broth (LB) nutrient medium and incubated for 1 hr at 30° C. This incubation makes it possible to initiate the desporulation of *Bacillus thuringiensis* spores which are converted into vegetative form and prolong the contact time with the substrate in order to check that no spores remain on the earthenware tile or aluminium plate.

For each of the tubes incubated at 30° C., a series of ten-fold (factors of 10) successive dilutions by volume is produced with liquid LB (dilution to 101 or to one hundred millionth). Finally, 1 ml is taken up into each of the tubes of each series of dilutions, and is then deposited onto the bottom of a sterile empty Petri dish. LB agar medium is then poured into the dish (inoculation throughout). The dishes are then placed in an incubator at 30° C. for approximately 20 hrs. The colonies are counted one by one and a mean live spore count is calculated. The decontamination factor may be calculated by determining the reduction in thousands of spores killed ($log_{10}$).

The results of these tests conducted on earthenware tile or aluminium plate are shown in FIGS. 4A and 4B. The foams according to the invention with 5% sodium hypochlorite and with 5% hydrogen peroxide are effective on earthenware tiles in 30 min. On aluminium plates, only bleach by way of disinfecting agent was tested and a foam according to the invention containing 5% sodium hypochlorite is also effective in 30 min on such a substrate.

III.4. Evaluation of Decontamination Efficacy of Foams on Vertical Wall.

Tests are conducted in order to determine the biocidal efficacy of NaOCl and $H_2O_2$ foams on a vertical wall. These tests are conducted according to the operating protocol described above with rectangular dishes and according to the formulations detailed above.

For these tests on a vertical wall, the foam applied forms a cone, the base whereof rests on the bottom of the dish and rises up the vertical wall. The contamination zone remains covered by the foam.

For the tests on a vertical wall, one test with the 5% NaOCl foam and two tests with a 5% $H_2O_2$ foam were conducted. The results of these tests are shown in FIG. 5. The 5% NaOCl and 5% $H_2O_2$ have physicochemical properties and a rate of action enabling them to have a sufficient contact time with the vertical wall to decontaminate the latter.

III.5. Evaluation of Decontamination Efficacy of Foams in Filling Mode.

Tests are conducted in order to determine the biocidal efficacy of NaOCl and $H_2O_2$ foams in filling mode. These tests are conducted according to the operating protocol described above with containers which may be rectangular dishes or tubes and according to the formulations detailed above. Contamination is performed on two of the vertical walls of the dish (50 µl of solution containing $10^8$ spores/ml on each wall) or on the vertical wall of the tube.

For the tests in filling mode, six tests with a 5% NaOCl foam, one test with a 7.5% NaOCl foam and five tests with a 5% $H_2O_2$ foam were conducted. The results of these tests are shown in FIG. 6. The various types of foam tests are suitable for decontaminating enclosed spaces in filling mode.

III.6. Evaluation of Decontamination Efficacy of Foams According to Moisture Percentage.

Tests are conducted in order to determine the biocidal efficacy of NaOCl and $H_2O_2$ foams at different moisture percentages. These tests are conducted according to the the biological operating protocol and according to the formulations detailed above.

The moisture percentage of the foam is modified following changes in foam generator settings. The generator is thus configured a first time to obtain foams with 2.5% moisture and a second time to obtain 3% moisture. A test was conducted with a NaOCl foam at 3.5% moisture and another at 4%. The same applied for an $H_2O_2$ for which a test was conducted at 2.7% and another at 2.8% moisture.

Figure 7:
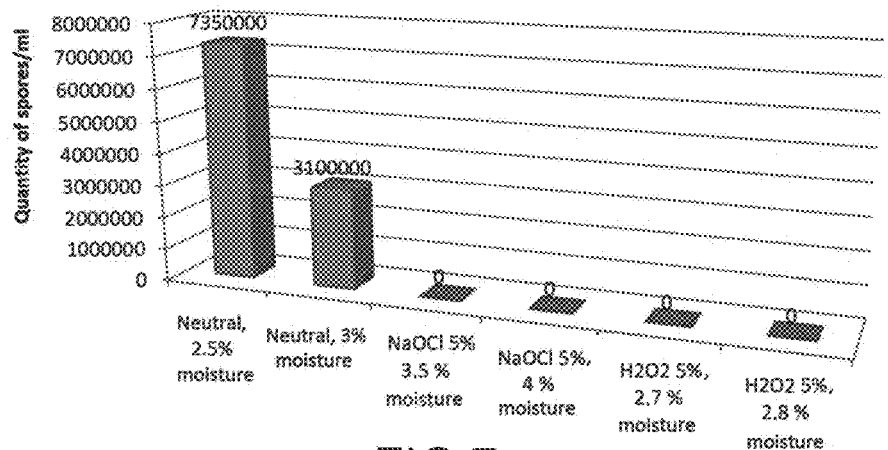

The results of these tests are shown in FIG. 7. The NaOCl foam is effective from 3.5% moisture (expansion 28.5) and the $H_2O_2$ from 2.7% moisture (expansion 37).

III.7. Evaluation of Decontamination Efficacy of Foams after Ageing of Solutions.

Tests are conducted in order to determine the biocidal efficacy of NaOCl and $H_2O_2$ foams after several weeks of storage. These tests are conducted according to the biological operating protocol and according to the formulations detailed above.

Tests are performed on the day of preparation of the solutions (t=0), 1 week after (t=1 wk), 2 weeks after (t=2 wk) and 5 weeks after the preparation thereof (t=5 wk). The initial liquid solutions from which the foams are produced are stored in a cold store at 4° C. for the ageing time.

Figure 8:
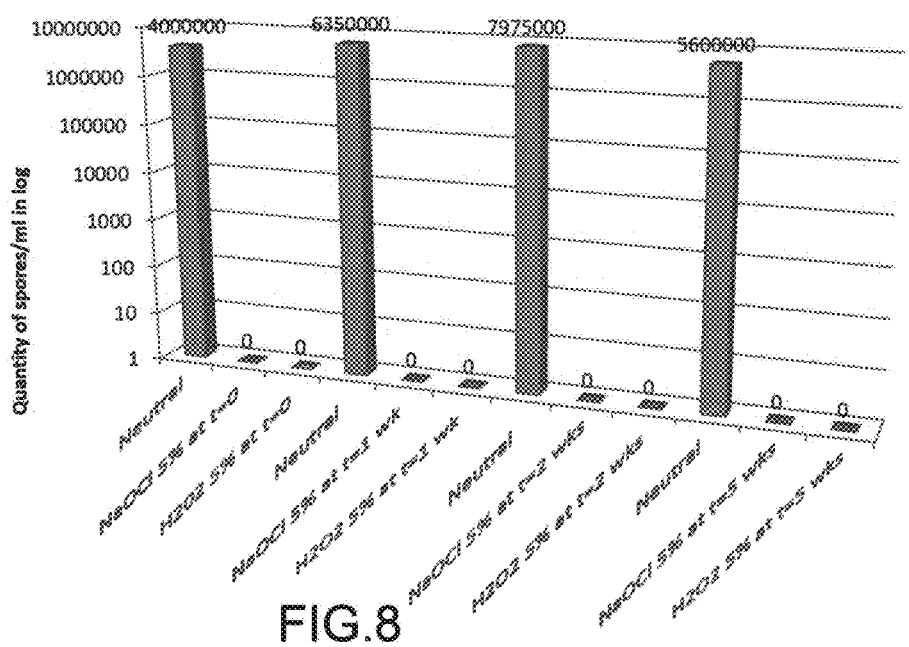
Figure 9A:
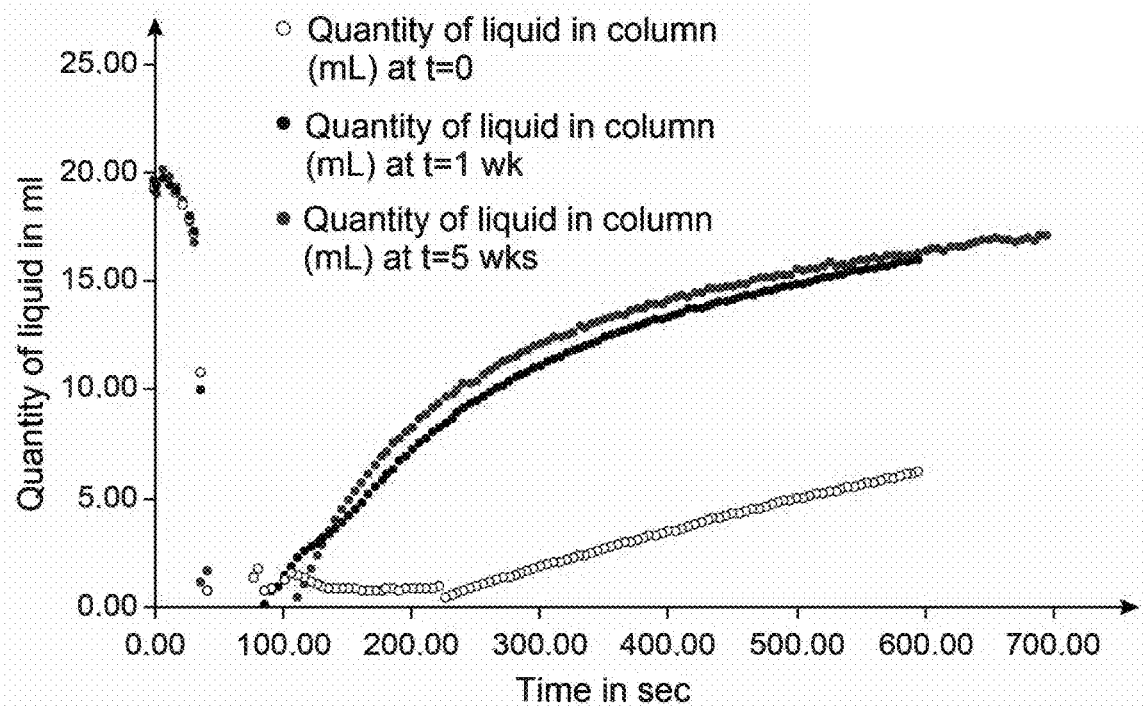
Figure 9B:
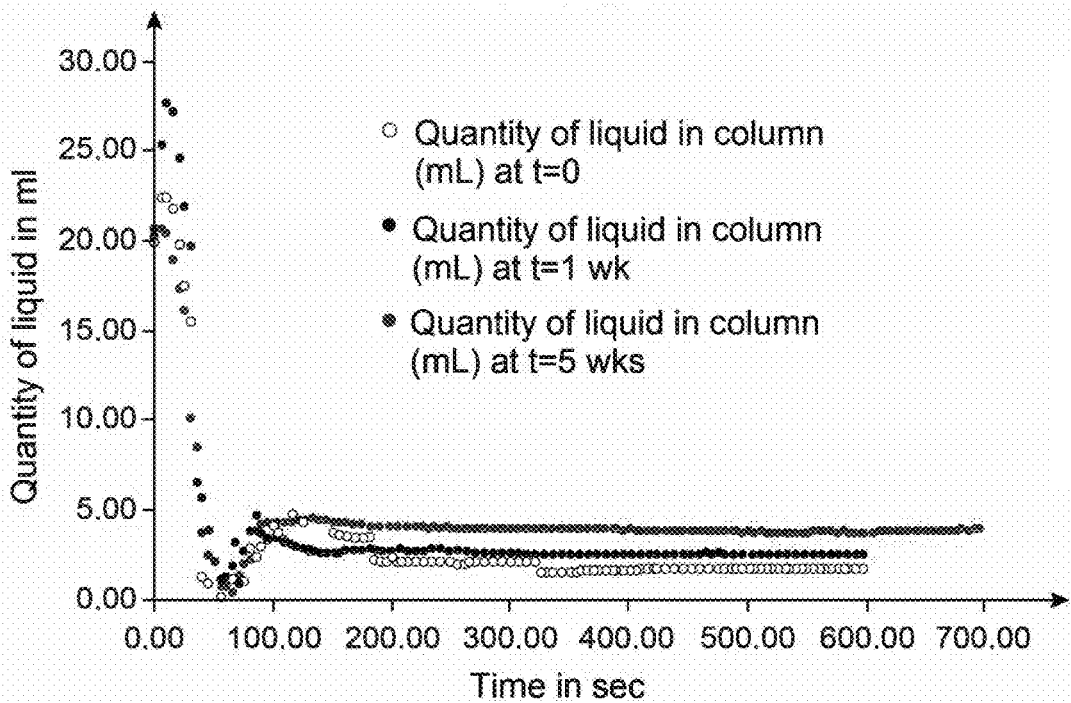
Figure 10:
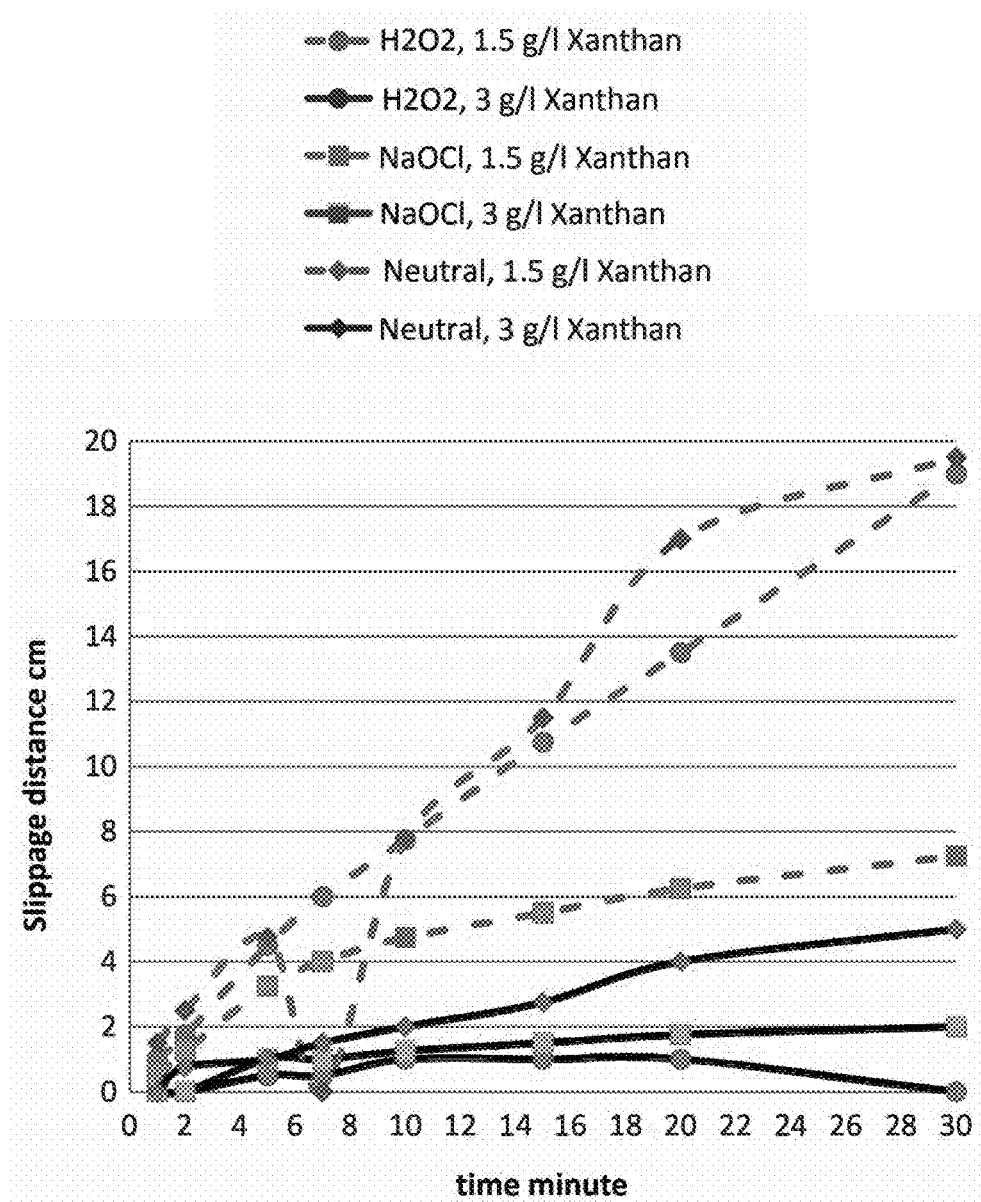

A test is conducted with a 5% NaOCl foam and a 5% $H_2O_2$ foam at each ageing time. The results of these tests are shown in FIG. 8. The foams retain Bt spore decontamination potential even after 5 weeks of storage of the initial foaming solution.

III.8. Evaluation of Foamability of Foaming Solutions and Stability Over Time of Corresponding Foams.

Foaming experiments are conducted in order to determine the foamability of the NaOCl and $H_2O_2$ after several weeks of storage. These experiments are conducted with a commercial apparatus called Foamscan from Teclis. It is used to measure, in a 150 ml column and with an initial solution volume of 20 ml, not only the foaming rate for a given air flow rate (determined at 100 ml) but also the stability of the foam by stopping air injection.

Therefore, a measurement is made, as a function of time, of the reduction in the quantity of liquid in the column until air injection is stopped (approximately 60 seconds, see FIGS. 9A and 9B). Then, from the time the gas is stopped, the quantity of liquid in the column increases more or less quickly, indicating the drainage of the foam and thereof the stability thereof.

In the presence of a viscosifying agent such as xanthan, a delay in the onset of drainage may be observed which is indicated by the existence of a plateau before the increase in the level of liquid in the column. The duration of this plateau indicates the stability of the foam. The ageing results obtained at t=0, t=1 wk and t=5 wk, are illustrated in FIG. 9.

As such, for the 5% sodium hypochlorite solution and a quantity of xanthan of 1.5 g/l (FIG. 9A), all the curves show an identical and total transfer (first part of the curve) of liquid into the foam. The decrease is linear indicating that all of the air injected is captured to form the foam. After switching off the air, the fresh foam (t=0 wk) exhibits a plateau of approximately 180 s, then drainage starts slowly: after 10 min, only 25% of the liquid has drained. After 1 week of storage, while the foamability is identical, the stability, on the other hand, is lower: the drainage delay plateau observed is merely 40 s and the drainage is more rapid (75% of liquid drains in 10 min). The decontamination efficacy tests demonstrated that the biocidal solution remains foaming and that the corresponding NaOCl foam remains active after 5 weeks of storage.

For the 5% hydrogen peroxide solution and a quantity of xanthan of 1.5 g/l (FIG. 9B), all the curves show an identical and total transfer (first part of the curve) of liquid into the foam. The decrease is linear indicating that all of the air injected is captured to form the foam. After switching off the air, all of the foams exhibit a drainage delay greater than 10 min. The $H_2O_2$ foams are more stable than the NaOCl foams.

III.9. Evaluation of the Adhesion of Foams on a Vertical Wall According to Different Xanthan Concentrations.

These tests are intended to determine the adhesion of foam deposits on a vertical wall by measuring the slippage of the foam over time. Foam deposits of 3 different sizes were carried out with different solutions according to the present invention and with different concentrations of xanthan which is the viscosifying agent of the formulation. For these tests, four xanthan concentrations are tested: 1.5 g/l, 2 g/l, 2.5 g/l and 3 g/l.

These tests are conducted with, as a substrate, a wipe-off marker whiteboard. This is a non-porous and very smooth material which makes it possible to conduct these tests under the most difficult conditions. The position of the deposit at t=0 is recorded and, after various times have elapsed, the slippage distance of the foam is measured.

The NaOCl and $H_2O_2$ foams adhere to the surface of a wipe-off marker whiteboard. The slippage of the foam is slowed down considerably (mean slippage of 3 cm in 30 min) when the xanthan concentration is increased to 3 g/l (FIG. 10).

III.10. Evaluation of Evaporation of Different Foams.

Tests are conducted in order to determine the evaporation rate of a layer of foam and the influence of the disinfecting agents thereon. These tests are conducted using a controlled-temperature and hygrometry climatic chamber. It consists of evaporating horizontally approximately 24 $cm^3$ (4 cm×4 cm×1.5 cm) of foam in a stainless steel boat while measuring the loss of mass over time, using a precision balance. The climatic chamber is set to a temperature of 22° C. and a relative humidity of 40%.

The foam is generated by a static generator with beads and deposited in the stainless steel boat. The latter is then placed in the balance situated in the climatic chamber. The balance is entirely enclosed. It indicates the mass of the foam contained in the boat, the boat having been previously calibrated. A software program is used to record, every 10 min, the mass measured by the balance in real time. A second software program is used to take photos inside the balance.

The foams generated for these tests are 5% NaOCl, 5% $H_2O_2$ and neutral foams with 1.5 g/l or 3 g/l of xanthan. The duration of the tests is overnight or over a weekend.

The results of these tests are shown in FIG. 11 with the tests for the neutral foams, NaOCl foams and $H_2O_2$ foams in FIGS. 11A, 11B and 11C, respectively. The evaporation rate is constant for at least 300 min then starts to decrease for a low foam mass. It is also observed that, with NaOCl foams (FIG. 11B), after evaporation, a residue of sodium chloride and sodium carbonate crystals remains, the mass whereof is low but measurable. By calculating the slope equation over the first 300 minutes (linear regression), it is observed that the directional coefficients of the slopes of all of the evaporation tests are relatively similar (mean −0.0019+/−0.0003), either with or without disinfectant and at both xanthan concentrations. A test with a layer of water was conducted and the evaporation displays the same kinetics. Therefore, the initial evaporation does not appear to be influenced by the foam formulation and corresponds to the water evaporation. For 1 g of foam spread over 4 cm by 4 cm and over a thickness of 1.5 cm, evaporation is performed on average in 9 hours.

These tests were supplemented by depositing a layer of 5% NaOCl foam deposited with a spatula on a plastic vertical surface contaminated with Bt spore spots. This experiment was conducted under a ventilated hood in which the air flow accelerates the evaporation rate.

The decontamination efficacy measurements on Bt spores, according to the biological operating protocol above, exhibit excellent efficacy (greater than $10^6$ inactivated spores).

As such, in 14 hours, the foam layer had entirely disappeared and the foam liquid evaporated. After evaporation, a thin, transparent film of glucopon and xanthan is observed, for each foam. Furthermore, for the NaOCl foam, small sodium chloride and sodium carbonate crystals resulting from the evaporation reaction are also observed.

III.11. Evaluation of Retrieval of Foam by Suction.

Foam retrieval tests by suction were conducted with a liquid suction machine.

For this purpose, a 1 to 3 cm thick layer of a foam according to the invention was applied by floating onto a vertical wall or a 30l container was filled with a foam according to the invention. In both applications modes i.e. floating or filling, the foam is suitable for suction.

REFERENCES

[1] EFT Holdings Inc. "MATERIAL SAFETY DATA SHEET NAME OF FINISHED SOLUTION: EasyDECON® DF200-531X" Alabama 2008. http://www.easydecon.com/easydecon/EasyDECON%20DF200%20MSDS.pdf

[2] Patent application U.S. Pat. No. 7,276,468 on behalf of Sandia Corporation, granted on 2 Oct. 2007.

[3] EFT Holdings Inc. "Performance Data" Alabama 2011. http://www.easydecon.com/easydecon/FactSheete248.html

[4] Allen Vanguard—CASCAD™ Decontamination Foam, 2009. http://reports.hms-online.org/ViewProduct.aspx?CategoryId=175&ProductId=721

[5] "Biological Agent Decontamination Technology Testing" U.S. EPA. Biological Agent Decontamination Technology Testing. U.S. Environmental Protection Agency, Washington, D.C., EPA/600/R-10/087, 2010.

[6] International application WO 2004/008463 on behalf of CEA and COGEMA, published on 22 Jan. 2004.

[7] "A quantitative kinetic theory of emulsion type, I. Physical chemistry of the emulsifying agent" Gas/Liquid and Liquid/Liquid Interface. Proceedings of the International Congress of Surface Activity (1957): 426-438.

[8] Regulation (EU) No. 528/2012 of 22 May 2012 concerning the provision on the market and use of biocidal products.

[9] International application WO 02/043847 on behalf of CEA, published on 6 Jun. 2002.

The invention claimed is:

1. A foam of a dispersion of gas bubbles in a foaming solution, consisting of, per litre of the solution:
   from 0.05% to 1.5% by weight of at least one foaming organic surfactant,
   from 0.05% to 0.8% by weight of at least one organic gelling or viscosifying agent,
   from 1% to 14% by volume of at least one disinfecting agent, and
   water,
   wherein the foam has an expansion between 20 and 50.

2. The foam according to claim 1, wherein the at least one foaming organic surfactant is selected from the group consisting of a non-ionic foaming surfactant, an anionic foaming surfactant, and a cationic foaming surfactant.

3. The foam according to claim 1, wherein the at least one organic gelling or viscosifying agent is selected from the group consisting of a water-soluble polymer, a hydrocolloid, a heteropolysaccharide, a cellulose derivative, and a polysaccharide.

4. The foam according to claim 1, wherein the at least one disinfecting agent is selected from the group consisting of a chlorinated product, an aldehyde, and an oxidant.

5. The foam according to claim 1, wherein
   from 0.1 to 1.1% by weight of the at least one foaming organic surfactant,
   from 0.15% to 0.3% by weight of the at least one organic gelling or viscosifying agent, and
   either from 2% to 7.5% by volume or from 5% to 14% by volume of the at least one disinfecting agent or of a mixture of disinfecting agents are present in the foaming solution.

6. The foam according to claim 1, wherein
   from 0.1 to 1.1% by weight of an alkylpolyglucoside,
   from 0.15% to 0.3% by weight of xanthan gum, and
   either from 2% to 7.5% by volume or from 5% to 14% by volume of sodium hypochlorite or hydrogen peroxide are present in the foaming solution.

7. A method for treating a surface contaminated with at least one biological agent, the method comprising:
   contacting the surface with the foam according to claim 1.

8. The method according to claim 7, wherein the surface is made of a metal, metal alloy, steel, tinplate, silicon, glass containing silicate, silica glass, ceramic, brick, porcelain, cement, concrete, asphalt, stone, granite, wood, clay, plastic or a combination thereof.

9. The method according to claim 7, wherein the biological agent is at least one species or bio-toxic element selected from the group consisting of a pathogenic spore, Gram negative bacteria, Gram positive bacteria, a toxin, and a virus.

10. The method according to claim 7, wherein the contacting is performed by:
    applying, on the surface, the foam by spraying or by floating or
    filling a structure containing the surface with the foam.

11. The method according to claim 10, further comprising: after the contacting,
    drying sprayed or floated foam by evaporation, or
    draining foam used in a filling mode.

12. The method according to claim 7, further comprising:
    after the contacting, either retrieving the foam by suction before complete drying or retrieving a dry residue of the foam by suction or by wiping.

* * * * *